(12) United States Patent
Kay

(10) Patent No.: US 7,707,046 B2
(45) Date of Patent: Apr. 27, 2010

(54) AUTOMATED PROCESSING OF ELECTRONIC MEDICAL DATA FOR INSURANCE AND DISABILITY DETERMINATIONS

(75) Inventor: Lay K. Kay, Pasadena, CA (US)

(73) Assignee: QTC Management, Inc., Diamond Bar, CA (US)

( * ) Notice: Subject to any disclaimer, the term of this patent is extended or adjusted under 35 U.S.C. 154(b) by 400 days.

(21) Appl. No.: 11/157,125

(22) Filed: Jun. 20, 2005

(65) Prior Publication Data
US 2007/0038480 A1 Feb. 15, 2007

Related U.S. Application Data

(63) Continuation-in-part of application No. 10/279,759, filed on Oct. 23, 2002.

(60) Provisional application No. 60/344,663, filed on Oct. 25, 2001, provisional application No. 60/345,998, filed on Oct. 24, 2001.

(51) Int. Cl.
G06Q 10/00 (2006.01)
G06Q 50/00 (2006.01)
A61B 5/00 (2006.01)
G06F 19/00 (2006.01)
G06Q 40/00 (2006.01)

(52) U.S. Cl. .................. 705/3; 705/2; 705/4

(58) Field of Classification Search .............. 705/2, 705/3, 4
See application file for complete search history.

(56) References Cited

U.S. PATENT DOCUMENTS

| 5,367,675 | A | * | 11/1994 | Cheng et al. ............... 707/2 |
|---|---|---|---|---|
| 5,613,072 | A | * | 3/1997 | Hammond et al. ............ 705/4 |
| 5,911,132 | A | * | 6/1999 | Sloane ........................ 705/3 |
| 6,003,007 | A | * | 12/1999 | DiRienzo ..................... 705/4 |
| 6,049,794 | A |  | 4/2000 | Jacobs et al. |
| 6,108,665 | A |  | 8/2000 | Bair et al. |
| 6,263,330 | B1 |  | 7/2001 | Bessette |
| 6,434,531 | B1 |  | 8/2002 | Lancelot et al. |
| 6,470,319 | B1 | * | 10/2002 | Ryan ........................... 705/1 |
| 6,581,038 | B1 |  | 6/2003 | Mahran |
| 6,604,080 | B1 |  | 8/2003 | Kern |
| 6,738,784 | B1 | * | 5/2004 | Howes .................... 707/104.1 |
| 6,988,088 | B1 |  | 1/2006 | Miikkulainen et al. |
| 7,191,451 | B2 | * | 3/2007 | Nakagawa ................. 719/317 |
| 7,260,480 | B1 |  | 8/2007 | Brown et al. |
| 2001/0041992 | A1 |  | 11/2001 | Lewis et al. |
| 2001/0044735 | A1 | * | 11/2001 | Colburn et al. ............... 705/4 |
| 2002/0035486 | A1 | * | 3/2002 | Huyn et al. ................... 705/3 |
| 2002/0046199 | A1 |  | 4/2002 | Scarborough et al. |
| 2002/0046346 | A1 | * | 4/2002 | Evans ....................... 713/200 |
| 2002/0069089 | A1 | * | 6/2002 | Larkin et al. ................. 705/4 |
| 2002/0091550 | A1 | * | 7/2002 | White et al. .................. 705/4 |
| 2002/0138306 | A1 |  | 9/2002 | Sabovich |
| 2003/0200123 | A1 | * | 10/2003 | Burge et al. .................. 705/4 |
| 2004/0122704 | A1 |  | 6/2004 | Sabol et al. |

(Continued)

*Primary Examiner*—Gerald J. O'Connor
*Assistant Examiner*—Amber L Altschul
(74) *Attorney, Agent, or Firm*—McDermott Will & Emery LLP

(57) ABSTRACT

Methods and systems are described for automated processing of medical data for insurance and disability determinations. Based on medical conditions claimed by a claimant, medical evidence queries are automatically generated to provide instructions to medical providers for conducting physical exams and laboratory tests and for retrieving medical records. After medical evidence is collected according to the queries, the medical evidence and related rating codes and decisions are displayed to rating personnel in a user-friendly format to assist in making a rating decision.

21 Claims, 26 Drawing Sheets

U.S. PATENT DOCUMENTS

2004/0122705 A1  6/2004  Sabol et al.
2004/0122707 A1* 6/2004  Sabol et al. .................... 705/2
2004/0122708 A1* 6/2004  Avinash et al. ................ 705/2
2004/0141661 A1  7/2004  Hanna et al.
2005/0033773 A1  2/2005  Roberge et al.
2005/0256744 A1  11/2005 Rohde et al.

* cited by examiner

Entry Screen

Claimant Name: _____ Last _____ First    Sex: ☐ M ☐ F

Age: ____    SSN: ___-___-___    Claim No. _____

Physician Name _____ Last _____ First    Specialty _____

| Claim Condition #1 ____ | Diagnosis: | | Diagnosis: | |
|---|---|---|---|---|
| | Diagnosis: | | | |
| | Condition: | | Condition: | |
| | Condition: | | Condition: | |
| | Condition: | | Condition: | |
| | Condition: | | Condition: | |
| | Condition: | | | |
| | Specific History: | | | |

| Claim Condition #2 ____ | Diagnosis: | | Diagnosis: | |
|---|---|---|---|---|
| | Diagnosis: | | | |
| | Condition: | | Condition: | |
| | Condition: | | Condition: | |
| | Condition: | | Condition: | |
| | Condition: | | Condition: | |
| | Condition: | | | |
| | Specific History: | | | |

Special Instructions to the Doctor

| | |
|---|---|
| Joint | Range of Motion must be included in every joint claim condition |
| Eyes | Include Goldman Chart and reading in report |
| Ears | Include pure tone audiometery and Maryland CNC Speech recognition results |
| Psych | Include current GAF scores in results |
| Cancer | Address cancer treatment such as chemotherapy, include beginning and end dates |
| PFT | Include both Pre- and Post- Bronchodilater results |
| Hypertension | If on anti-hypertensive therapy, include 3 blood pressure readings on 3 consecutive days |
| Functional | State functional limitations on daily living |

Questions

| | | |
|---|---|---|
| Question 1: | | |
| Question 2: | | |
| Question 3: | | |
| Question 4: | | |

*FIG. 6*

 PHYSICIAN EXAM PROTOCOL ©

Dear Dr.Kay:

Range of motion must be included on every joint condition.

PHYSICAL EXAMINATION:

VITAL SIGNS:

Height _____ Weight _____

Pulse _____ Blood Pressure <u>Must have Three readings</u> 1 _____ 2 _____ 3. _____

Any claimed condition is high blood pressure, and the claimant is not on blood pressure medication, please record the blood pressure two more times on two separate days and record below:

Date _____ Blood pressure reading 1 ____ 2 ____ 3 ____
Date _____ Blood pressure reading 1 ____ 2 ____ 3 ____

HEENT:

EYES: PLEASE INCLUDE FUNDISCOPIC EXAMINATION

✚ normal    ✚ Abnormal Describe _____

SKIN:

Is there any scar present? (Including surgical scar) ✚No ✚Yes If yes answer the following question:

Location: _____ Size length x width _____ x _____ Cm

| | | | | | | |
|---|---|---|---|---|---|---|
| Cause by | ✚ Injury | ✚ surgery type: | | ✚ disease type: | | |
| Shape | ✚ round | ✚ oval | ✚ linear | ✚ irregular | Texture | ✚ soft | ✚ firm |
| Tenderness | ✚ absent | ✚ present | | | Surface | ✚ elevated | ✚ depressed |
| Color | ✚ dark | ✚ pale | ✚ pink | ✚ blank with skin | Adherence | ✚ No | ✚ Yes |

Underlying tissue loss    ✚ No   ✚ Yes   Describe: _____
Disfigurement    ✚ No   ✚ Yes   Describe: _____
Keloid formation    ✚ No   ✚ Yes   Describe: _____
Limitation of function    ✚ No   ✚ Yes   Describe: _____

HEART:
✚WNL ✚ Abnormal Describe: _____

According to the New York Heart Association scale the claimant is:
  ✚No restriction       ✚ marked limitation of the activities but comfortable at rest
  ✚ slight limitation of the activities     ✚ dyspnea at rest

MUSCULOSKELETAL SYSTEM:

Lower Extremities

Leg length from ant. superior iliac spine to the medial malleolus: Right _____ cm Left _____ cm Examine feet for any sign of abnormal weight bearing
✚ no sign    ✚ abnormal weight bearing sign present
      ✚ callosities      Where: _____
      ✚ breakdown      Where: _____
      ✚ unusual shoe wear pattern    Describe: _____
      ✚ other abnormal weight bearing    Describe: _____

*FIG. 7A*

Does the Veteran require:

+ no devise    + brace    + corrective shoes

+ crutches    + cane    + other: _____

Why? _____

The Posture of the Claimant is:  + normal  + abnormal

Describe: _____

Gait    + normal    + abnormal

Describe: _____

Does the Claimant have limited function of standing and walking?

+ No    + Yes Describe: _____

The appearance of the Knee joint is: +WNL +Abnormal Which side? +Right +Left +Both Can be describe as below:

| Heat | Redness | Swelling | Effusion | Drainage | Abnormal Movement | Instability | Weakness |
|------|---------|----------|----------|----------|-------------------|-------------|----------|
| + | + | + | + | + | + | + | + |

Please record the joint involved including the prosthetic joint, if applicable with goniometer as follow:

| Joint Name | Movement | Normal ROM | Right | | | Left | | |
|---|---|---|---|---|---|---|---|---|
| | | | Ankylosis In Degree | Active ROM | Pain In Degree | Ankylosis In Degree | Active ROM | Pain In Degree |
| Knee | Flexion | 0-140 | | | | | | |
| | Extension | 0 | | (–) | (–) | | (–) | (–) |
| | TEST | Normal | Right | | | Left | | |
| | | | WNL | Abnormal | | WNL | Abnormal | |
| | Drawer Test | < 5min | + | + | | + | + | |
| | McMurray's Test | | + | + | | + | + | |

NOTE: For knee joint extension more than "0" should be address as "–", example if the joint movement is 10-140, then flexion is 140 degree and extension is –10 degree.

DELUCA ISSUE: Is the range of motion of the effected joint additionally limited by:

| Joint Name | None | Pain | Fatigue | Weakness | Lack of Endurance | Incoordination | If More Than One, Which One Has The Major Function Impact |
|---|---|---|---|---|---|---|---|
| Right Knee | + | + | + | + | + | + | |
| Left Knee | + | + | + | + | + | + | |

Does the Claimant have any constitutional signs of arthritis (such as anemia, weight loss, fever, skin disorder, etc.)

+ No    + Yes    Describe: _____

RECTAL EXAMINATION:

Evidence of:  + fissure    Location: _____    + ulceration   Location: _____

+ fecal leakage    How often? ____ Pad needed? + NO    + Yes How many pad/day? ____

+ hemorrhoids    If present, you MUST answer the following questions:
Location: _____

Reducible?    + No    + Yes

Evidence of bleeding?    + No    + Yes

Thrombosed?    + No    + Yes

*FIG. 7B*

Palpation of rectal wall  + normal  + abnormal  Describe: _____
Prostate:  + normal  + enlarged  Describe: _____

NEUROLOGICAL EXAMINATION:

Cranial Nerve Exam I-XII:  + WNL  + abnormal  Describe: _____

SUMMARY - CRANIAL NERVE EXAMINATION
| | | | |
|---|---|---|---|
| I | Examine smell in each nostril (Call for smell test sheet, if applicable) | VIII | Examine hearing and perform Rinne's and Weber's tests |
| II | Examine visual acuity, visual field, fundus and pupillary light response | IX | Examine pain sensation in the tonsillar fossae |
| III, IV, VI | Examine eye movements and near reaction. Check for nystagmus. | X | Examine palatal movement plus the gag reflex |
| V | Examine motor and sensory innervation plus the jaw jerk and the corneal response | XI | Examine sternomastoid and the upper fibres of the trapezius |
| VII | Examine the muscles of facial expression (plus buccinator) and taste over the anterior two-thirds of the tongue (Call for taste test sheet, if applicable) | XII | Examine tongue movements and appearance |

Upper Extremities
Motor
function  + WNL  + Abnormal

Muscle name: ____  ____  ____
Power 5/5

| Motor Strength Classification | |
|---|---|
| 5 | No motor deficit |
| 4 | Active movement against gravity, resistance |
| 3 | Active movement against gravity only |
| 2 | Active movement with gravity eliminated |
| 1 | Slight contraction and no movement |
| 0 | No contraction |

Muscle atrophy?  +No  + Yes  If yes where? _____

Sensory  + WNL  + Abnormal  Describe: _____
Reflexes  + WNL  + Abnormal  Describe: _____

Lower Extremities
Motor  +WNL  + Abnormal

Muscle name: ____  ____  ____
Power 5/5

| Motor Strength Classification | |
|---|---|
| 5 | No motor deficit |
| 4 | Active movement against gravity, resistance |
| 3 | Active movement against gravity only |
| 2 | Active movement with gravity eliminated |
| 1 | Slight contraction and no movement |
| 0 | No contraction |

Muscle atrophy?  +No  + Yes  If yes where? _____

Sensory  + WNL  + Abnormal  Describe: _____
Reflexes  + WNL  + Abnormal  Describe: _____

*DIAGNOSTIC TEST*

Final results for all diagnostic tests performed inside or outside of your office must be included in your report. We will not accept any report that indicates diagnostic tests are pending. A report indicating tests pending will serve as an incomplete report and be returned to the physician for completion. Reports returned will not meet our turnaround time requirement. Again, if you need any diagnostic test, please call for authorization and conduct the test. Do not recommend the test...Do the test.

Chest x-ray result _____
UA result _____
CBC Test result _____
EKG result _____

*FOR CLAIMANT'S CLAIMED CONDITION* hypertension

+ No Diagnosis because      + The condition resolved
                             + There is no pathology to render a diagnosis
+ Unable to make a diagnosis because _____
+ The diagnosis is: _____

*FIG. 7C*

Subjective factors:
Objective factors:

FOR CLAIMANT'S CLAIMED CONDITION seizure disorder

+ No Diagnosis because    + The condition resolved
                          + There is no pathology to render a diagnosis
+ Unable to make a diagnosis because _____
+ The diagnosis is:

Subjective factors:
Objective factors:

FOR CLAIMANT'S CLAIMED CONDITION knee problems

+ No Diagnosis because    + The condition resolved
                          + There is no pathology to render a diagnosis
+ Unable to make a diagnosis because- _____
+ The diagnosis is:

Subjective factors:
Objective factors:

FOR CLAIMANT'S CLAIMED CONDITION hemorrhoids

+ No Diagnosis because    + The condition resolved
                          + There is no pathology to render a diagnosis
+ Unable to make a diagnosis because _____
+ The diagnosis is:

Subjective factors:
Objective factors:

Describe the effects of the condition on the claimant's: _____
Usual occupation:
Daily activity:

Does the Claimant's GI condition cause significant malnutrition?
+ No        + Yes because of _____

Does the Claimant's GI condition cause significant anemia?
+ No        + Yes because of _____

| Question |
|---|
| Answer : |

*FIG. 7D*

 CLAIMANT QUESTIONNAIRE ©

Name: JOHN DOE      Date: _____   Phone: _____
Age: 57   CLM# 123456789      Sex: + Male   + Female Dear Mr. JOHN DOE:                                                                          1371
In order for Dr. KAY to have complete and accurate information to examine you, please fill out the attached form completely. Answer all the questions asked (if not applicable, write "N/A") and bring this with you to your appointment. Thank you.

If you have any questions regarding the form or require assistance completing it, please call 1-800-555-5555 for assistance.

*GENERAL INFORMATION*
Please complete the following table for the condition(s) listed.

| Work Sheet # | Condition | Date of Onset | Date of Diagnosis | How was the diagnosis determined? | Is it due to injury? YES | NO |
|---|---|---|---|---|---|---|
| 8040 | hypertension | | | | + | + |
| 15050 | seizure disorder | | | | + | + |
| 2040 | Knee problem | | | | + | + |
| 9060 | hemorrhoids | | | | + | + |
| | | | | | + | + |

According to the condition listed in the table above, please describe chronologically the course of the condition:

*SPECIFIC HISTORY FOR knee problem*

What kind of joint problem you have? _____   How long you have it? _____

Name the joint(s) involved including left/right: _____

Currently, do you suffer from the following symptoms from your joint condition?

| Symptom | Yes | No | Symptom | Yes | No | Symptom | Yes | No |
|---|---|---|---|---|---|---|---|---|
| Pain | + | + | Swelling | + | + | "Locking" | + | + |
| Weakness | + | + | Inflammation | + | + | Fatigue | + | + |
| Stiffness | + | + | Instability | + | + | Lack of endurance | + | + |
| Recurrent Subluxation | + | + | Dislocation | + | + | | | |

*FIG. 8A*

Briefly describe your symptoms:

Do the symptoms for your joint condition occur:
+ Constantly     + Flare-up off and on How severe is your flare-up? + mild + uncomfortable + distressing + horrible + excruciating How often does it flare-up? _____ Lasts how long? _____
(daily, monthly, twice a year, etc.)          (minutes, days, weeks, etc.)

What makes the flare-up occur?
(over usage, play handball, etc.)

What alleviates the flare-up?
(If medication give name, rest, etc.)

Describe how the flare-up effects your ability to perform your daily function.

Do you have constitutional symptoms of your joint condition? (Such as – anemia, weight loss, fever, skin disorder, etc):

+ No     + Yes     Describe: _____

Did/do you receive treatment and/or surgery for your joint condition? + No + Yes  Please complete the table below:

| Type | Name | How often | Date | Response | | | Side Effects/Complication after Surgery | | |
|---|---|---|---|---|---|---|---|---|---|
| | | | | Good | Same | Poor | N | Y | If yes, describe below: |
| Medicine | | | | + | + | + | + | + | |
| Medicine | | | | + | + | + | + | + | |
| Treatment | | | | + | + | + | + | + | |
| Surgery | | | | + | + | + | + | + | |
| Surgery | | | | + | + | + | + | + | |

Do you have any prosthetic implants? + No + Yes -- Answer the following questions:

| Date of Implant | Joint Name | Pain | | Weakness | | Limitation of Motion | | Need any | | |
|---|---|---|---|---|---|---|---|---|---|---|
| | | No | Yes | No | Yes | No | Yes | Crutch | Brace | None |
| | | + | + | + | + | + | + | + | + | + |
| | | + | + | + | + | + | + | + | + | + |

SPECIFIC HISTORY FOR seizure disorder

Do you suffering from +epilepsy or +narcolepsy?    For how long? _____    Number of attacked past 12 month: _____

How does the frequency of the past year compare to previous years?

+ Increase    Describe: _____

+ Decrease    Describe: _____

+ No change

*FIG. 8B*

+ Not able to identify because usually fluctuates - Describe: _____

+ Other    Describe: _____

How does your disease affect your daily activity?  Describe:
```
┌─────────────────────────────────────────────────────────────┐
│                                                             │
│                                                             │
│                                                             │
└─────────────────────────────────────────────────────────────┘
```

Describe the current symptoms for your condition:
```
┌─────────────────────────────────────────────────────────────┐
│                                                             │
└─────────────────────────────────────────────────────────────┘
```

The symptoms you describe above occur:

+ constantly     + off and on -- If off and on, please complete the table below.

| How often? | How long each time? | Factors which cause it to occur | Factors which relieve it? (If medication, write name) | What is your function level during the flare-up period? |
|---|---|---|---|---|
|  |  |  |  |  |

Did/do you receive treatment and/or surgery for your neurological condition?

+ No     + Yes --  Please complete the table below (If you need more space, use the back of the sheet.)

| Name of the Medication or Treatment | How often | Date | Response | | | Side effects | | If yes what is the side effect? |
|---|---|---|---|---|---|---|---|---|
|  |  |  | Good | Same | Poor | No | Yes |  |
|  |  |  | + | + | + | + | + |  |
|  |  |  | + | + | + | + | + |  |
|  |  |  | + | + | + | + | + |  |

SPECIFIC HISTORY FOR hemorrhoids

What kind of anorectal problem do you have?  _____ For how long? _____

Do you have problems holding your stool?
+ No     + Yes

How frequent are the fecal leakages? _____

Is a pad needed?    + No    + Yes    If yes how many pad per day? _____

Do you have hemorrhoids?
+ No     + Yes

Do your hemorrhoids bleed?
    + No    + Yes
        How often? _____

*FIG. 8C'*

Do your hemorrhoids thrombose (blood clot inside)?
✢ No   ✢ Yes
　　How often? _____
　　Does it stay out all of the time?   ✢ No   ✢ Yes Describe the current symptoms from your rectal condition:

|  |  |
| --- | --- |
|  |  |

Currently do you receive any treatment for your rectal condition? ✢ No ✢ Yes Please complete the table below:

| Type | Name | How often | Date | Response | | | Side Effects/Complication after Surgery | | |
| --- | --- | --- | --- | --- | --- | --- | --- | --- | --- |
|  |  |  |  | Good | Same | Poor | N | Y | If yes, describe below: |
| Medicine |  |  |  | ✢ | ✢ | ✢ | ✢ | ✢ |  |
| Medicine |  |  |  | ✢ | ✢ | ✢ | ✢ | ✢ |  |
| Surgery |  | ■ |  | ✢ | ✢ | ✢ | ✢ | ✢ |  |
| Surgery |  |  |  | ✢ | ✢ | ✢ | ✢ | ✢ |  |

SPECIFIC HISTORY FOR hypertension
Do you have high blood pressure?
✢ No   ✢ Yes Date of diagnosis: _____
　　Any symptoms:   ✢ No   ✢ Yes. Describe: _____

Currently do you receive any treatment for your hypertension? ✢ No ✢ Yes   Please complete the table below:

| Name | Date | Side effects | | |
| --- | --- | --- | --- | --- |
|  |  | No | Yes | If yes what is the side effect? |
|  |  | ✢ | ✢ |  |
|  |  | ✢ | ✢ |  |
|  |  | ✢ | ✢ |  |
|  |  | ✢ | ✢ |  |

Are you able to do the following activities: (Y = Yes, N = No)

| Activity | Y | N | Activity | Y | N | Activity | Y | N | Activity | Y | N | Activity | Y | N | Activity | Y | N |
| --- | --- | --- | --- | --- | --- | --- | --- | --- | --- | --- | --- | --- | --- | --- | --- | --- | --- |
| Brush teeth | ✢ | ✢ | Shower | ✢ | ✢ | Vacuum | ✢ | ✢ | Drive car | ✢ | ✢ | Take out trash | ✢ | ✢ | Climb stairs | ✢ | ✢ |
| Dress self | ✢ | ✢ | Cook | ✢ | ✢ | Walk | ✢ | ✢ | Shop | ✢ | ✢ | Push lawn mower | ✢ | ✢ | Garden | ✢ | ✢ |

If you can't perform all the activities above, why?

|  |
| --- |
|  |

Your usual occupation is _____ How long? _____
Are you currently employed?   ✢ No   Date of last employment: _____
　　　　　　　✢ Yes   ✢ Same job   ✢ Different job   What type? _____

*FIG. 8D*

PREVIOUS DIAGNOSTIC TESTS
List the diagnostic tests you have undergone for all of your medical conditions. This will help to speed-up the processing of your case. *(Such as MRI, endoscopy, cardiac catheterization, etc.)* If you need additional space, use the back side of this page

| Name of Test | Date Performed | Ordering Doctors: | | Facility Performing the Test: | | |
|---|---|---|---|---|---|---|
| | | Name | Phone # | Name | Address | Phone |
| | | | | | | |
| | | | | | | |
| | | | | | | |
| | | | | | | |

*FIG. 8E*

SPECIFIC HISTORY FOR  *right knee patellofemoral syndrome*

*Name the diagnosis for the condition listed above:*  [The claimant has been suffering from right knee patellofemoral syndrome]

*How long has the condition existed?*   *Since* [1980]   *or*   [   ] *months or* [   ] *years*

*Describe below how and when the*   *Right knee*   *condition occurred:*

[and it occurred when he fell on his right knee during his training exercise.]

*Is it due to injury?*   ○ *No*   ● *Yes*

*Briefly describe the symptoms of the*   *Right knee*   *condition:*

[The symptoms of the condition are pain since 1980 with weakness and stiffness.]

*Do the symptoms described above occur*
  ○ *Constantly*   ● *Flare-up off and on*
    *As often as* [2] *times per* ○ *day* ● *week* ○ *month*
    *And each time last for* [3] *hours or* [   ] *days or* [   ] *weeks*

*Does the*   *Right knee*   *condition require bed rest and treatment by a physician?*
  ● *No*   ○ *Yes, as often as* [   ] *per* ○ *month or* ○ *Year. It last for* [   ] *days*

*Briefly describe the current treatment and/or any medications taken for the*   *Right knee*   *condition.*

[The current treatment is Motrin during flare ups which gives him relief.]

*Any prosthetic implants?*
  ● *No*   ○ *Yes and the prosthesis had been implanted since* [   ] *or for* [   ] *years*
    *Which joint?* [   ]
    *Any symptoms from the implant?*
      ○ *No*   ○ *Yes. Please check the approiate symptoms below:*
        ☐ *Painful motion of the implanted joint*
        ☐ *Weakness of the implant joint*
        ☐ *Other* [   ]

JACK SMITH, M.D.
Internal Medicine & Cardiology    DRAFT
10101 1st ST.
Summerfield, CA 90101

CLAIMANT:          John Doe
CLAIM NUMBER:      123456789
DATE OF EXAM:      7/15/2002
date of report:    7/18/2002

GENERAL HISTORY:

SPECIFIC HISTORY FOR right knee patellofemoral syndrome

The claimant has been suffering from right knee patellofemoral syndrome since 1980. The condition is due to injury and it occurred when he fell on his right knee during his training exercise. The symptoms of the condition are pain since 1980 with weakness and stiffness. The symptoms described above occur intermittently as often as 2 times per week, and each occurrence lasts for 3 days. He stated his condition does not cause incapacitation. The current treatment is Motrin during flare ups which gives him relief. He has not had any prosthetic implants of the joint.

SPECIFIC HISTORY FOR low back condition, status post fusion

The claimant has been suffering from low back condition status post fusion for 21 years. The symptoms of the condition is pain on and off since 1977. He describes the first occasion of back pain while in Germany in 1977. At that time, he was accidentally jerked off of a tank by a heavy chain and thrown to the ground and injured his back. He also described how he was jumping off an onto tanks 20 to 25 times a day and jumping over toe-bars many times a day during the entire time that was in the Tank Corpos from 1970 to 1980. He described back pain and aches and even continuing while he was in Korea, while he was at Fog Hood, Texas. At that time, the pain radiated to his legs with numbness. Currently, he complains only of on and off pain. In 2002, he underwent lumbar spine fusion after multiple modalities of treatment including injections while he was in Fort Hood, Texas, Germany and Alaska. The pain does not travel to other parts of the body. The symptoms described above occur intermittently as often as 1 times per month, and each occurrence lasts for 4 days. He stated his condition does not cause incapacitation. For his condition he has undergone the following tests at the following facilities before: MRI on April 2002 by Dr. Jack Smith at White Facility

SPECIFIC HISTORY FOR asthma

The claimant has been suffering from asthma for 3 years. The condition affects body weight from 193 pounds to 180 pounds within 3 months period. He did not have any treatment to correct his weight. From his respiratory condition, he has shortness of breath after walking three city blocks. He also complains of slight difficulty in breathing when climbing stairs, and the description is shortness of breath with activity as described above. The symptomatology is relieved using Albuderol inhaler. He stated he is asthmatic and the attacks occur as frequently as 1 times per month. He needs to visit a physician to control the attacks as often as 3 times per month. He said he did not contract infection easily from his respiratory condition. He stated he has not suffered from respiratory failure. He requires bronchodilator by mouth intermittently.

| DIAGNOSTIC CODE SUMMARY - RIGHT KNEE |||||
|---|---|---|---|---|
| Name: John Doe | | Examiner: Kramer, Debbie |||
| Claim #: 589654999 | | Date of the Examination: 07/15/2002 |||
| Main Category | Sub Category | Finding || Rating Code |
| Disease | Causes | Injury || 5010 |
| | Frequency | Intermittently || 5003 |
| Physical Exam | Right Flexion | 130 degrees<br>Pain at 100 degrees || 5260 |
| | Left Flexion | 140 degrees || 5261 |
| | Right Extension | 0 degrees || 5261 |
| | Left Extension | 0 degrees || 5261 |
| | Deluca Right | Pain<br>Major functional impact at 100 degrees || 5261 |
| | Deluca Left | No Deluca issue || 5261 |
| | Instability | Drawer Rt. | Normal | 5257 |
| | | Drawer Lt | Normal | |
| | | McMurray Rt | Normal | |
| | | McMurray Lt | Normal | |
| Complication | Prosthesis | Absent || 5055 |

*FIG. 10*

| Entry Screen | | | | | |
|---|---|---|---|---|---|

| Claim Number | 123456789 | |
|---|---|---|

| Name of Claimant | John Doe | | | | |
|---|---|---|---|---|---|
| Claim Number | 123-45-6789 | SSN | 123-45-6789 | Application Date | |

| Source of Medical Evidence | Date of the Medical Evidence |
|---|---|
| Dr. Lay K. Kay | 09/01/00 |

| | Type of Claim | | |
|---|---|---|---|

| | Diagnostic Code | | |
|---|---|---|---|
| | Musculoskeletal | Part | Right Knee |
| | Diagnosis | | S/P removal of semilunar cartilage of the right knee with osteoarthritis changes |

| | Diagnostic Code | | |
|---|---|---|---|
| | Musculoskeletal | Part | Lumbar Spine |
| | Diagnosis | | Lumbar spine sprain |

*FIG. 11A*

| RIGHT KNEE RATING OPTION | | | |
|---|---|---|---|
|   | 5002 | Rheumatoid arthritis |   |
| X | 5003 | Degenerative arthritis |   |
|   | 5055 | Prosthesis of the knee |   |
|   | 5256 | Ankylosis of the knee |   |
|   | 5257 | Impairment of the knee |   |
| X | 5258-5259 | Semilunar cartilage |   |
| X | 5260-5261 | Knee Range of Motion |   |

*FIG. 11B*

| SEMILUNAR CARTILAGE OF THE RIGHT KNEE | | | | | |
|---|---|---|---|---|---|
| Description | | | Reason | Source | Date |
| 5258 | | Dislocated semilunar cartilage | | Dr. Lay Kay | 09/01/00 |
| | | Frequent episodes of 'locking' pain | | | |
| | | Effusion into joint | | | |
| Rating | | % | | | |

| 5259 | X | Removal of semilunar cartilage symptomatic | He underwent a semilunar cartilage removal in April 1978. After the operation, he still suffers from the symptom of pain and swelling | Dr. Lay Kay | 09/01/00 |
|---|---|---|---|---|---|
| Rating | 10 | % | | | |
| 5259 | | S/P removal of semilunar cartilage of the right knee with osteoarthritis changes | | | |

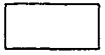

*FIG. 11C*

| RIGHT KNEE ROM | | | | | |
|---|---|---|---|---|---|
| Description | | | Reason | Source | Date |
| 5260 | Flexion | 20 | The flexion of the right knee is 20 | Dr. Lay Kay | 09/01/00 |
| Rating | 30 | % | | | |
| | | | S/P removal of semilunar cartilage of the right knee with osteoarthritis changes | | |
| 5261 | Extension | 0 | | Dr. Lay Kay | 09/01/00 |
| Rating | 30 | % | | | |
| | | | | | |
| | Pain in range of motion | | | Dr. Lay Kay | 09/01/00 |
| Rating | | % | | | |

*FIG. 11D*

| LUMBAR SPINE RATING OPTION | | | | |
|---|---|---|---|---|
| | 5003 | | Degenerative arthritis | |
| | 5285 | | Fracture of the vertebra | |
| | 5289 | | Ankylosis of the lumbar spine | |
| X | 5292 | | Range of motion of lumbar spine | |
| X | 5293 | | Intervertebral disc syndrome | |
| X | 5293 | | Lumbosacral strain | |

*FIG. 11E*

| LUMBAR SPINE ROM | | | | | |
|---|---|---|---|---|---|
| Description | | | Reason | Source | Date |
| 5292 | Flexion | 70 | The range of motion of the lumbar spine flexion is 70 with pain at 90, extension is 15 with pain at 90, right lateral is 25 with pain at 90, left lateral is 40 with pain at 90, right rotation is 30 with pain at 90, and the left rotation is 35 with pain at 90. | Dr. Lay Kay | 09/01/00 |
| | Extension | 15 | | | |
| | Right Lateral | 25 | | | |
| | Left Lateral | 40 | | | |
| | Right Rotation | 30 | | | |
| | Left Rotation | 35 | | | |
| Rating | 10 | % | | | |
| 5292 | | Lumbar spine sprain | | | |

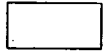

*FIG. 11F*

| Final Rating | | | | | | | | |
|---|---|---|---|---|---|---|---|---|
| Diagnostic Code | | | Diagnosis | SC/NSC | | Rating | | Effective Date |
| 5259 | | | S/P removal of semilunar cartilage of the right knee with osteoarthritis changes | Service Connected | | 10 | | December 1972 |
| 5260 | | | S/P removal of semilunar cartilage of the right knee with osteoarthritis changes | Service Connected | | 30 | | December 1972 |
| 5292 | | | Lumbar spine sprain | Service Connected | | 10 | | December 1972 |
| The total combined rating is: | | | | | | 40 | | December 1972 |
| After review and correction, the information is final | | | | | | ✚ Accept | | ✚ Reject |

*FIG. 11G*

Name: John Doe
Claim Number: 123-45-6789                    SSN: 123-45-6789

The original claim of the claimant with diagnosis of S/P removal of semilunar cartilage of the right knee with osteoarthritis changes and lumbar spine sprain is Service Connected because the veteran was in Germany and sustained knee and back injuries.

The 09/01/00 C & P examination by Dr. Lay K. Kay on the knee presented with symptoms of pain, stiffness, swelling. The range of motion of the right knee (in degree) shows flexion at 20 with pain at 20, and with the extension at 0. The range of motion of the right knee is also affected by pain. The range of motion of the left knee (in degrees) shows flexion at 140 with the extension at 0.
He also underwent semilunar cartilage removal surgery in April 1978 with the residual symptom of pain and swelling.

Based on the 09/01/00 C & P examination by Dr. Lay K. Kay, the diagnosis of the lumbar spine was reported as lumbar spine sprain with the symptom of radiation of pain down to the right leg. On examination, the findings were muscle spasm present over the right side of the spine and the straight leg raising test was positive on the right. The range of motion of the lumbar spine (in degrees) is: flexion 70, extension 15, right lateral bending 25, left lateral bending 40, right rotation 30, left rotation 35.

*FIG. 11H*

AUTOMATED PROCESSING OF ELECTRONIC MEDICAL DATA FOR INSURANCE AND DISABILITY DETERMINATIONS

REFERENCE TO RELATED APPLICATIONS

The present application is a continuation-in-part of and claims priority benefit under 35 U.S.C. §120 from U.S. patent application Ser. No. 10/279,759, filed Oct. 23, 2002, which claims priority benefit under 35 U.S.C. §119(e) from U.S. Provisional Application No. 60/344,663, filed Oct. 25, 2001, and U.S. Provisional Application No. 60/345,998, filed Oct. 24, 2001, each of which is hereby incorporated herein by reference in its entirety.

BACKGROUND OF THE INVENTION

1. Field of the Invention

The present invention relates to methods and systems for gathering and processing medical data to support rating decisions in the adjudication of insurance and disability requests.

2. Description of the Related Art

Government agencies and insurance companies have developed rules for adjudication of insurance or disability requests. Examples of insurance or disability programs include the Department of Veterans Affairs (VA) program, the Social Security Disability Insurance program, the Workers' Compensation program, various property and casualty insurance programs, and so forth.

In order to adjudicate a request made by a claimant, certain medical evidence is required. Medical evidence requirements refers to requirements of information about a claimant that is relevant to the medical conditions claimed by the claimant, such as the age and gender of the claimant, physical examination data, laboratory test data and medical history data pertinent to the claims, and so forth. The requirements are specified by rules developed by the government agency or by the insurance company, pertinent case law, government regulations, legislation and administrative decisions, and so forth. For example, the requirements may specify that if a claimant claims a certain medical condition, a medical provider must conduct certain physical examinations and laboratory tests on the claimant or ask certain questions. The requirements may also specify, for example, that a claimant must have a range of motions less than a certain degree to claim a limb disability. Requirements can also be specified by conventional medical knowledge, for example requiring a certain test to confirm a particular claimed condition.

The rating rules are normally documented in manuals that may have many different titles, herein referred to as "rating books." A rating code refers to a classification used by the government agency or insurance company that typically refers to a medical condition or a class of medical conditions in a rating book. The collection of rating rules, rating codes, pertinent legislation and case law for an insurance or disability program is herein referred to as the "rules collection" for that program. The rating rules may include rules on how to make a rating decision based on the collected medical evidence and the rating codes. For example, in a V.A. disability program, the rules collection typically specifies a disability percentage range based on rating codes and collected medical evidence. A V.A. rating personnel reviews the rating codes and medical evidence, and specifies a disability percentage within the range.

In a disability or insurance request process, the claimant typically visits a hospital, clinic or medical office. A medical provider such as a physician or a nurse collects medical evidence from the claimant to support a rating decision. The rating decision is typically made by the government agency or the insurance company based on the medical evidence collected by the medical provider and based on the rules collection. The medical providers are typically provided with documents generally referred to as "physician's disability evaluation" or "medical examination handbooks" to assist them with collecting medical evidence. The handbooks are herein referred to as "medical handbooks". The medical handbooks typically contain the medical evidence requirements for the rules collection.

Whereas the rating books are typically intended for the rating personnel in the government agency or insurance company, the medical handbooks are typically intended for the medical providers. Although they are somehow related, the rating books and medical handbooks typically contain very few direct cross-references. In addition, the medical providers often are not familiar with the rules collection of the insurance or disability program, and make mistakes in using the medical handbooks. Therefore, the required medical evidence can be omitted or entered incorrectly, thus affecting the making of a correct rating decision. In addition, the rating personnel, who typically have only limited medical knowledge, must spend considerable time to review the medical information collected by the medical providers. What is desired is an automated system that provides instructions to medical providers to collect medical evidence based on the rules collection of the insurance or disability program. What is also desired is a system that provides supporting information in a user-friendly format to assist rating personnel in making a rating decision based on the collected medical evidence.

In many cases, a claimant makes claims for multiple medical conditions. The conventional practice is to complete a medical evidence document for each claimed condition. This results in significant duplication of effort as duplicate medical data is gathered and identical medical procedures might be conducted multiple times. Therefore, what is desired is a system that eliminates the duplications.

To better illustrate the drawbacks of conventional practices and the need for better systems, the VA Compensation and Pension (C&P) program is described as an example. This government program provides payments of benefits to military veterans for medical disability resulting from their military service. The rating rules are included in the Code of Federal Regulations 38-CFR, the governing legislation, and in a rating book. The related medical handbook is a series of documents titled Automatic Medical Information Exchange (AMIE) worksheets. These worksheets specify the medical evidence required and the procedures to be utilized for each claimed condition included in 38-CFR. There are currently over fifty separate AMIE worksheets covering a wide array of claims, from a Prisoner of War Protocol Examination to Scars Examination. Each worksheet is designed as a stand-alone medical document for the particular claimed disability. In addition to the AMIE worksheets, legislatively mandated requirements, administrative requirements, and court ordered information have, from time to time, specified other medical evidence or dictated the manner in which it is to be collected. Significant training and experience is required to familiarize medical providers with the worksheets and the additional requirements. Significant delays and extra cost in claims processing are encountered when required medical evidence is not provided or incorrect procedures are conducted. Additionally, the claimant frequently claims multiple disabilities. These can number up to twenty or more claims for one claimant. The current practice is to complete an AMIE worksheet with all the requirements for each claimed disability. This results in unnecessary duplication of procedures with the entailed extra costs and time.

SUMMARY OF THE INVENTION

One aspect of the invention relates to a computer-implemented method of assisting the collection of medical evidence for adjudication of a medical disability request. At least one claim of a medical condition is received by a claimant into a storage. Based on the at least one claim and based on a disability rules collection, a plurality of medical evidence queries are automatically generated. Medical evidence data is received from a first electronic data storage into a second storage, said medical evidence data being responsive to at least one of the generated medical evidence queries.

Another aspect of the invention relates to a computer-implemented method for facilitating adjudication of a medical disability request. Medical evidence data concerning a claimant is received. A disability rating report is automatically generated based on the medical evidence data. The medical evidence data is preferably obtained by a method comprising the following steps. At least one claim by a claimant of a medical condition is received into a first storage. A plurality of medical evidence queries is automatically generated based on the at least one claim and based on a disability rules collection. Answers to the generated medical evidence queries from an electronic data storage are received into a second storage, said answers corresponding to the medical evidence data.

Still another embodiment relates to a computer system comprising a computer-readable medium having stored thereon computer-executable instructions for performing the following method. At least one claim of a medical condition is received from a claimant. A plurality of medical evidence queries is generated based on the at least one claim and based on a disability rules collection. Medical evidence data corresponding to the generated medical evidence queries is received from an electronic data storage.

Yet another embodiment relates to a computer-readable medium having stored thereon computer-executable instructions for performing the following method. At least one claim of a medical condition is received from a claimant. A plurality of medical evidence queries is generated based on the at least one claim and based on a disability rules collection. The generated medical evidence queries are displayed in at least one data collection protocol.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

FIG. 6 illustrates one embodiment of a data entry form for claimed medical conditions.

FIGS. 7A-7D illustrate one embodiment of a medical provider's exam protocol.

FIGS. 8A-8E illustrate one embodiment of a claimant questionnaire.

FIGS. 9A-9B illustrate one embodiment of a narrative medical report.

FIG. 10 illustrates one embodiment of a diagnostic code summary medical report.

FIGS. 11A-11H illustrate one embodiment of a rating report.

DETAILED DESCRIPTION OF THE PREFERRED EMBODIMENTS

To better illustrate the invention, certain embodiments of the invention are described below in connection with the drawings. It should be understood that the scope of the invention is not limited by these embodiments but defined by the claims.

Overview of Disability Benefits Claims System

Figure 1:
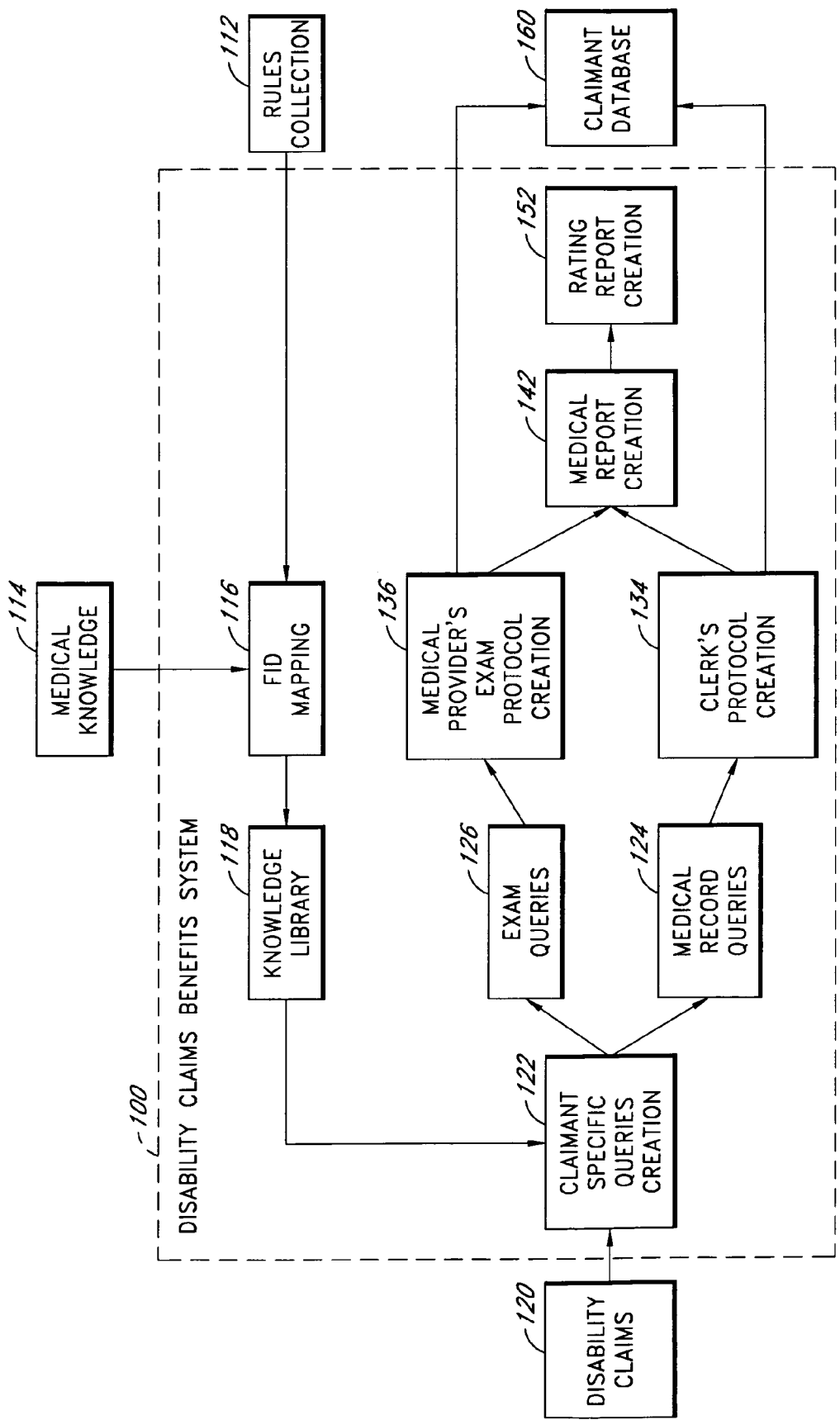
FIG. 1 illustrates the general overview of one embodiment of a disability benefits claims system.

FIG. 1 illustrates the general overview of one embodiment of a disability benefits claims system 100. The rules collection 112 for the insurance or disability program and pertinent medical knowledge 114 are organized by a FID mapping component 116 into a knowledge library 118. Based on the claimed medical conditions 120 from a claimant and based on the rules collection or medical knowledge stored in the knowledge library 118, the claimant-specific query creation module 122 creates claimant-specific medical evidence queries.

The queries are then separated into medical record queries 124 for medical records, and exam queries 126 for physical exams and laboratory tests. The medical record queries 124 for medical records may be used by the clerk's protocol creation component 134 to create a clerk's data collection protocol to collect the required data from medical records. Alternatively, the medical record queries 124 may trigger an electronic records querying component (not shown) that facilitates the collection of the required data from electronic medical records (EMR) stored in the claimant database 160.

The exam queries 126 for exams and tests may be used by the medical provider's exam protocol creation component 136 to create a medical provider's data collection protocol to assist a physician, nurse or technician in reviewing and extracting data from charts, radiological study results, nuclear medicine laboratory results, present medication, allergy and chronic condition lists (e.g., from medical alert bracelets) and other medical records of the patient. The exam protocol creation component 136 may also be used to create a medical provider's data collection protocol to assist the medical provider in conducting histories of the present illness, past medical histories, family and social histories, a review of systems, physical exams, laboratory tests, interviews with friends and family of the claimant, and interviews of the claimant's prior medical providers. The component 136 may also use the exam queries 126 to create a questionnaire to be answered by the claimant. The medical report creation component 142 uses the medical evidence collected from exams, tests, reviews, histories, interviews, claimant questionnaires and medical records to create a medical report. The rating report creation component 152 creates a rating report to assist rating personnel in adjudicating the claims. The collected medical evidence can also be stored in the claimant database 160.

Organizing Rules Collection into Knowledge Library

Still referring to FIG. 1, component 112 represents the rules collection for the insurance or disability program, typically embodied in rating books, legislation, administrative decisions and case law. Component 114 represents pertinent medical knowledge, such as instructions to a physician, lab technician or nurse for performing a physical exam or laboratory test. The rules collection and medical knowledge are organized by a FID mapping component 116 into FIDs and stored in a knowledge library component 118.

In a preferred embodiment, every unit of data that may be required by the rules collection for making a rating decision is identified by a field identification number (FID). Examples of FID data fields include a "patient name" field, a "heart rate" field, a "impaired limb motion range" field, and so forth. Each general medical evidence query is identified by a FID. A general medical evidence query corresponds to a medical evidence requirement specified by the rules collection or by medical knowledge. A claimant-specific medical evidence query is generated from the general medical evidence queries and based on the claimant's claimed medical conditions. Claimant-specific queries are described in the subsection titled "Generating claimant-specific medical evidence queries".

In a preferred arrangement, each FID includes a category code, a rating code and a data query code, separated by the underline symbol "_". For example, a FID can take the form of "H047_SM500_T001". The category code "H047" identifies the FID to a category of queries concerning the right knee. The rating code "SM500" identifies the FID to a particular rating code for musculoskeletal injuries in a rating book. The data query code "T001" identifies the FID to the data query "What is the range of motion?." In another example, the FID mapping number is "TK10_TS6600_T001". The category code "TK10" represents a category of queries concerning bronchitis. The rating code "TS6600" represents a rating book rating code "6600". The data query code "T001" represents the query "What is the FEV1 value?." A query text table stores the data query codes and the query text for each of the data query codes. The table may also store a long instruction text for each data query code as an instruction or explanation. The stored query text and long instruction text can be later displayed in a medical provider's exam protocol, history or interview protocol, claimant questionnaire, clerk's data collection protocol, medical report or rating report.

A FID can take other forms. For example, in a relational database arrangement, a rating code table can store the rating code for each data query code, and a category code table can store the category code for each data query code. Therefore a FID need only include a data query code, and the rating code and category code for the FID can be identified by referencing the rating code table and the category code table. In an object-oriented arrangement, a FID can be an object that includes a data query object field, a rating code object field and a category code object field.

The FID mapping component 116 organizes the rules collection into a plurality of FIDs. For example, for a rating code that identifies diabetes in a V.A. rules collection, the component 116 creates a plurality of FIDs, with each FID identifying a unit of medical evidence required for making a rating decision on the diabetes claim. Each FID preferably includes a category code, the V.A. rating code that identifies diabetes, and a data query code. For example, one FID includes a data query code representing the data query "Have you served in the Vietnam War?" because V.A. rules assume that Vietnam veterans' diabetes conditions are caused by exposure to Agent Orange. As described above, the data query code may be further associated with a long instruction text "If claimant has served in Vietnam and suffers from diabetes, assume that service connection exists."

Arrangement of Modules and Sub-Modules, Categories and Sub-Categories

Figure 2:
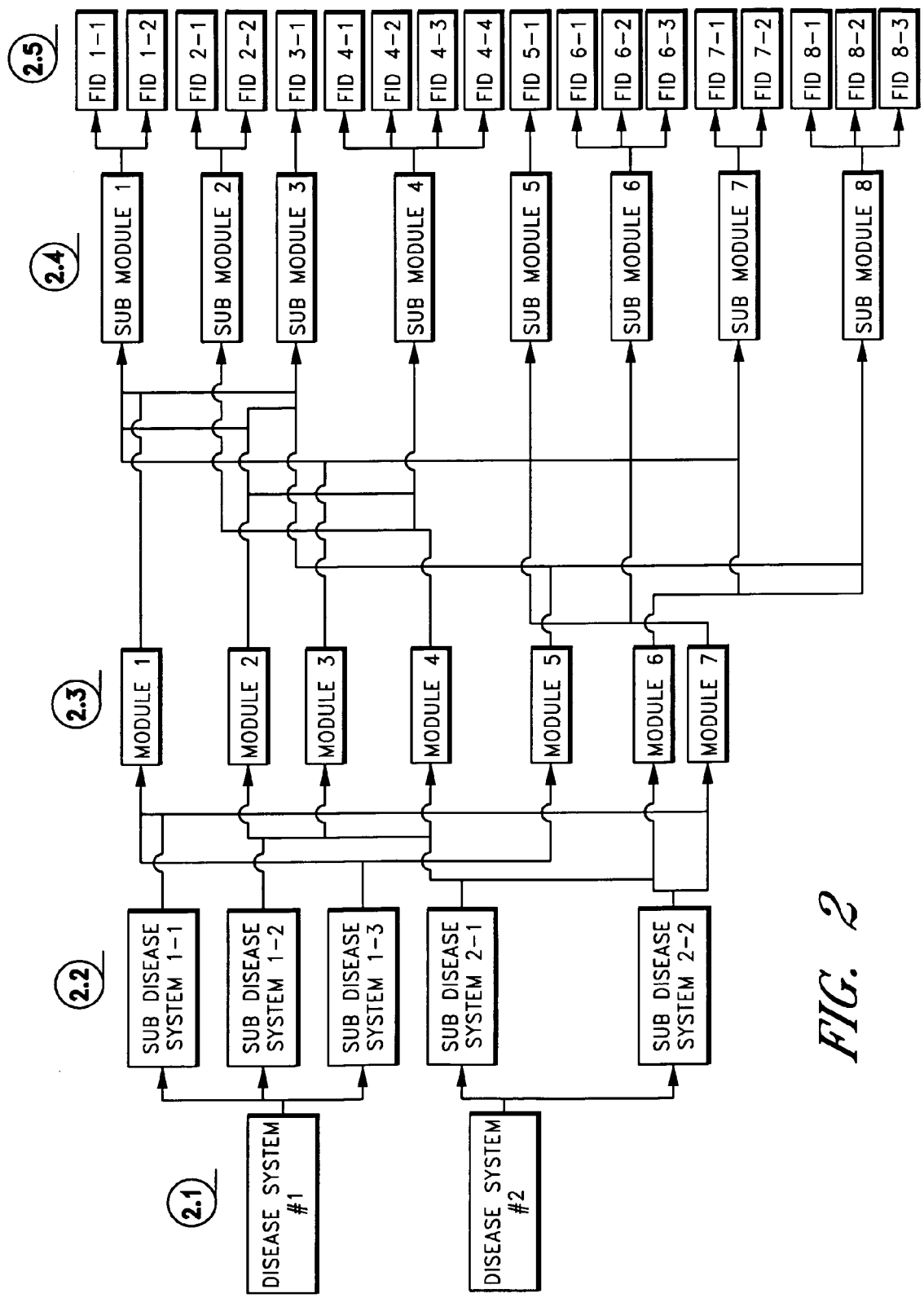
FIG. 2 illustrates one embodiment of an arrangement of modules and sub-modules.

FIG. 2 illustrates one embodiment of a disability benefits claims systems 100 that includes modules and sub-modules. A rating book typically classifies medical conditions into disease systems, also called body systems. Typical disease systems may include the cardiovascular system, the respiratory system, infectious diseases, and so forth. Some rating books classify a disease system into one or more sub-disease systems or sub-body systems. For example, a "cardiovascular disease system" may include sub-disease systems such as myocardial-infarction sub-disease system, arrhythmia sub-disease system, and so forth. A sub-disease system is typically unique to one disease system and is not shared by multiple disease systems.

As shown in FIG. 2, each sub-disease system is mapped to one or more modules of the disability benefits claims system 100. A module represents a function within the sub-disease system. For example, the lung sub-disease system can be mapped to a "history of symptoms" module, a "history of general health" module, a "physical examination of the lungs" module, and so forth. In one embodiment, sub-disease systems can share common modules. In one embodiment, modules are assigned priority numbers that identify a priority order among the modules.

Each module can include one or more sub-modules. For example, a "vital signs" sub-module can include data about the height, weight, pulse, and blood pressure of the claimant. A sub-module includes one or more FIDs. Modules can share common sub-modules. For example, the "vital signs" sub-module can be shared by multiple modules because vital signs information is needed for the diagnosis of many diseases and conditions. In one embodiment, sub-modules are assigned priority numbers that identify a priority order among the sub-modules.

A sub-module includes one or more FIDs. For example, the "vital signs" sub-module includes a "height" FID, a "weight" FID, a "pulse" FID and a "blood pressure" FID. In a preferred embodiment, each FID belongs to only one sub-module. In one arrangement, each FID includes a sub-module code that identifies the sub-module of the FID. In another embodiment, a sub-module table in the knowledge library 118 stores the FIDs for each sub-module.

In other embodiments, modules and sub-modules are not introduced. Each rating code and its general medical evidence queries directly correspond to a collection of FIDs. The FID collections for two rating codes may share one or more FIDs.

Figure 3:
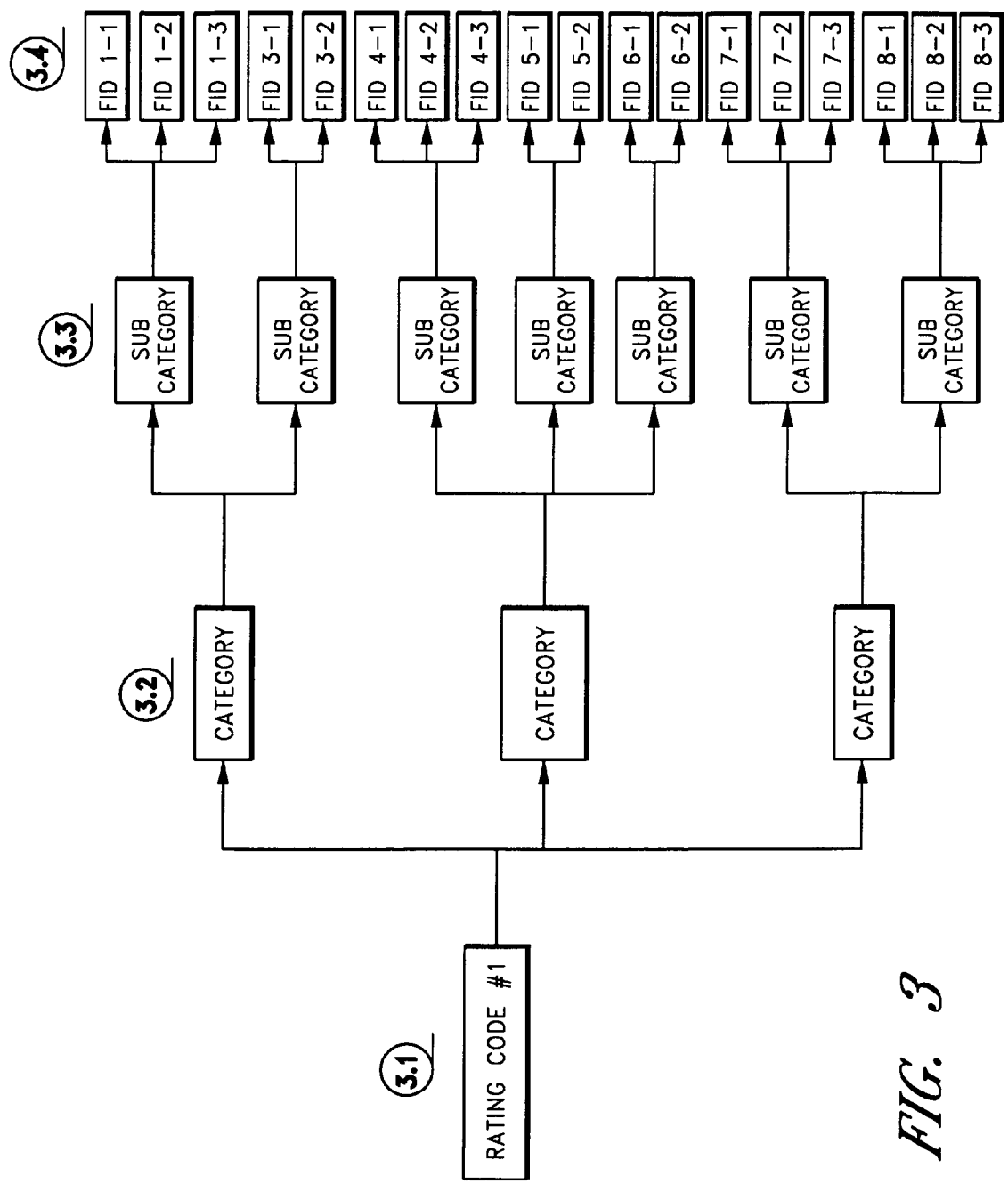
FIG. 3 illustrates one embodiment of an arrangement of categories and sub-categories.

Referring to FIG. 3, the unique data elements that make up the rules collection are grouped by category and sub-category. The categories and sub-categories preferably relate to classifications in the rating books. For example, categories can include "General", "Complications", "Function", "Symptoms", "Tests", and so forth. A category can be further classified into one or more sub-categories. For example, the "Function" category includes the sub-categories "ability" and "restriction". The "Tests" category can include sub-categories "confirmation," "essential," "indication," and "results." A sub-category includes one or more FIDs.

Figure 4:
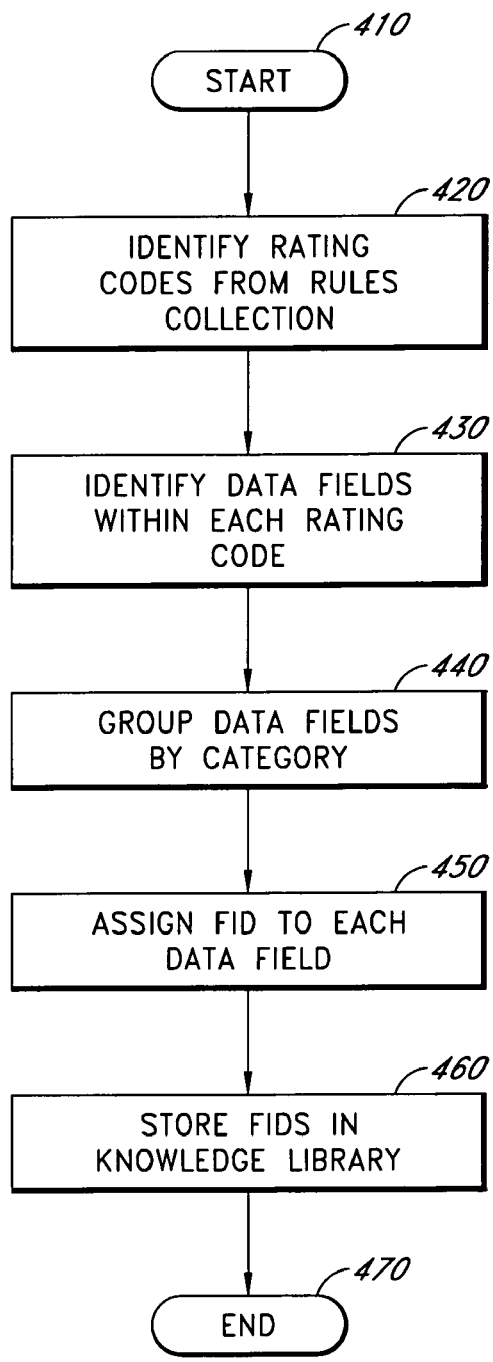
FIG. 4 illustrates one embodiment of a process of organizing rules collection into a knowledge library.

FIG. 4 illustrates one embodiment of a process of organizing rules collection into FIDs. From a start block 410, the process proceeds to a block 420 to identify rating codes from the rating books for the disability or insurance program. The process then proceeds to a block 430 to identify data fields within each rating code. Each data field represents a general medical evidence query. Data fields may also be identified based on pertinent medical knowledge, for example the knowledge of a experienced physician that certain medical evidence are needed to make a rating decision for a particular rating code. Data fields may also be identified based on case law and administrative decisions, for example the Deluca case and required "Deluca issues."

The process then proceeds to a block 440 to group the data fields by category. In another embodiment, data fields are grouped by sub-category. The process proceeds to a block 450, where a FID is assigned to each data field. In a preferred embodiment, a category code, a rating code and a data query code is assigned to each FID. The category code represents the category the data field is grouped into. The rating code represents the rating code for the data field. The data query code represents the data query for the medical evidence query. The process then proceeds to a block 460 to store the FIDs in a knowledge library component 118. The process terminates at an end block 470.

Generating Claimant-Specific Medical Evidence Queries

Figure 5:
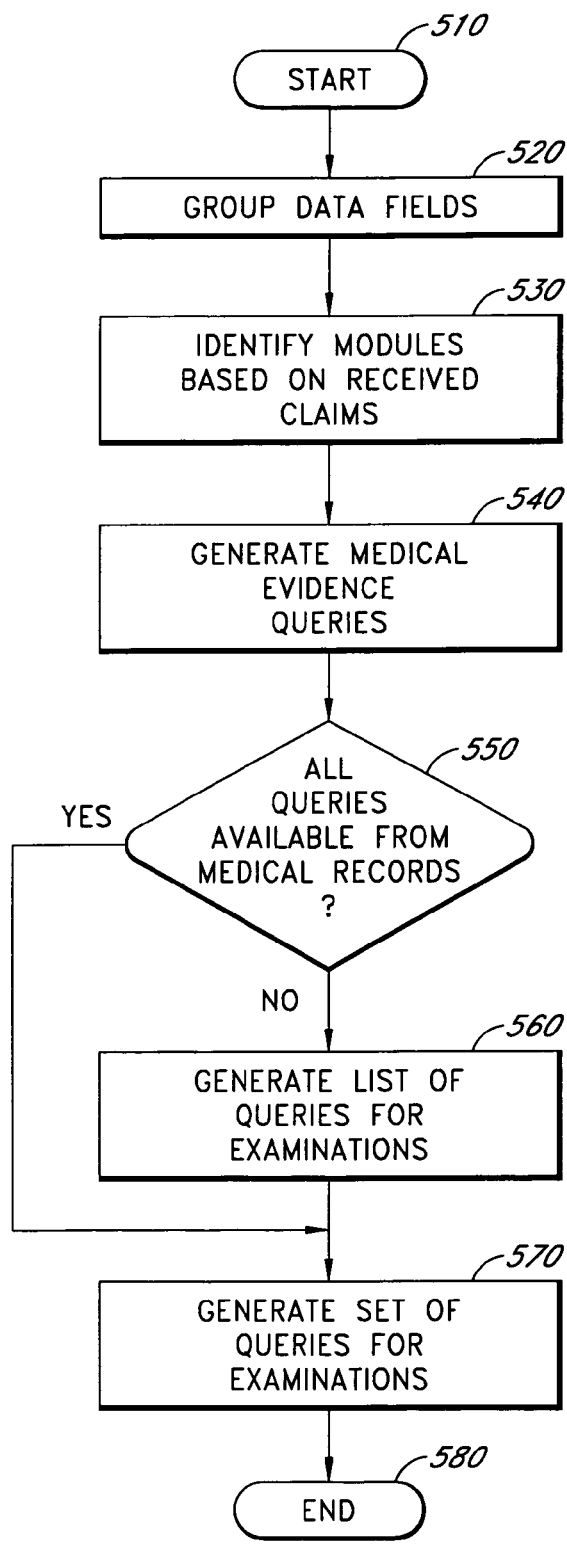
FIG. 5 illustrates one embodiment of a process of generating claimant-specific medical evidence queries.

In FIG. 1, the claimant-specific query creation module 122 receives the claimed medical conditions 120 from the claimant, and creates claimant-specific medical evidence query based on the claims and by referring to the general medical evidence queries stored in the knowledge library 118. As would be well-understood by those of skill in the art, the claimed medical conditions 120 might comprise physical, psychiatric, substance abuse disorders or other abnormalities, and are typically stored in any of a variety of computer-readable storage media. FIG. 5 illustrates one embodiment of the query-creation process.

Referring to FIG. 5, the process starts from a start block 510 and proceeds to a block 520, where the query creation component 122 receives one or more claims of medical conditions from the claimant. In one embodiment, the component 122 also receives other information provided by the claimant, for example information such as claimant name, age, gender filled out by the claimant on a data entry form. FIG. 6 is an example data entry form. It can be filled out by the claimant or by a clerk. The "Special Instructions to the Doctor" section displays special instructions retrieved from the knowledge library 118 for the particular insurance or disability program and displayed as a reminder to the medical provider.

Referring back to FIG. 5, at a block 530, the component 122 identifies the related modules based on the received claims. For example, if the claimed condition is "loss of eyesight," the component 122 may identify a "physical exam" module and a "neurological exam" module. The relationships of medical conditions and related modules are stored in the knowledge library 118. The component 122 also identifies all sub-modules of the identified modules. If two of the identified modules share common sub-modules, the duplicate sub-modules with the lower priority numbers are removed. From all of the FIDs that belong to the identified modules, the duplicate FIDs can also be removed. In other embodiments, instead of identifying the related modules based on the received claims, the component 122 identifies the related sub-modules, the related categories, or the related sub-categories. In another embodiment, the component 122 directly identifies the related FIDs stored in the knowledge library 118 based on the received claims.

At a block 540 of FIG. 5, the component 122 selects those FIDs in the knowledge library 118 that belong to the identified modules and sub-modules. The selected FIDs form a set of the claimant-specific medical evidence queries. The set can be stored in a variety of formats, for example as a text string with FIDs separated by field delimiters such as colons or semicolons, as a text file with a FID in each line, as a table with each FID as a record, as a series of objects with each FID having a "next FID" pointer that points to the next FID object, and so forth. This set of queries is preferably stored in a computer-readable storage, such as hard disk storage, solid state RAM, etc, and this data storage may be implemented using any type of computer storage device or devices, and using any type or types of data repositories (e.g., relational databases, flat files, caches, etc.).

In one embodiment, the component 122 compares the information already received from the claimant, and fills the related FIDs with such information. For example, if the claimant has provided his or her name, age and gender, the component then fills the related FIDs with the claimant-provided information. The details of filling a FID with collected medical evidence are described below in more detail.

From the block 540, the process proceeds to a block 550, where the component 122 determines which of the generated claimant-specific queries may be satisfied from medical records. In another embodiment, a human operator reviews the generated queries and determines which of the queries may be satisfied from medical records. In still another embodiment, the component 122 accesses a claimant's EMR and determines which generated claimant-specific queries may be satisfied from the EMR. In other embodiments, instead of determining on a per FID basis, the determination can also be made on a per module, per sub-module, per category or per sub-category basis.

If all generated queries may be obtained from medical records, electronic or paper-based, then the process proceeds to block 570. Otherwise the process proceeds to a block 560, where the component 122 generates a set of claimant-specific queries to be satisfied from physical exams, histories and interviews, claimant questionnaires, laboratory tests, or other medical provider input. At the block 570, the component 122 generates a set of queries whose results can be obtained from existing medical records. The claimant-specific queries generated at the block 540 are thus separated into two sets of queries. In another embodiment, the queries generated at the block 540 are separated into three sets: one set of queries to be satisfied from physical exams, histories, interviews and claimant questionnaires, another set to be satisfied from laboratory tests, and a third set to be satisfied from medical records.

Referring back to the blocks 530 and 540 of FIG. 5, when the claimant submits claims for multiple conditions, it is possible that some of the modules are identified more than once by the claims. The component 122 searches for duplicate modules and eliminates such duplications. In other embodiments, the component can also search for and eliminate duplications on the sub-module or FID level.

Each module is associated with a priority number stored in the knowledge library 118. In the case where multiple modules are called that examine the same sub-disease system, the duplicate modules with the lower priority numbers are eliminated. In another embodiment, each FID is associated with a priority number stored in the knowledge library 118.

In one embodiment, the generated queries can be updated by a human operator. For example, a medical provider or rating personnel reviews the generated claimant-specific queries and adds, modifies or deletes one or more queries. This allows some flexibility and human control in the system 100. The human operator can also change the order of generated claimant-specific queries determined by the priority numbers.

The component 122 also checks special rules stored in the knowledge library 118 for exceptions and updates. Exceptions and updates are typically caused by changes in legislation, case law, and insurance or disability program rules. For example, special rules that represent the Deluca case decision can be stored in the knowledge library 118. The stored Deluca special rules can be associated with FIDs, categories or modules stored in the knowledge library 118. When the generated claimant-specific queries include a FID associated with a special rule, the special rule is retrieved from the knowledge library 118 and applied to include a special rule instruction with the FID, or to add, modify or remove other claimant-specific queries. The special rule can also change the order of generated claimant-specific queries determined by the priority numbers.

Creating Medical Provider's and Clerk's Data Collection Protocols

Referring back to FIG. 1, based on the generated set of claimant-specific queries for exams, the medical provider's protocol creation component 136 may create a medical provider's data collection protocol, also called a physician's exam protocol. The component 136 may also create a claimant questionnaire based on the claimant-specific queries. Based on the generated set of claimant-specific queries for medical records, the clerk's protocol creation component 134 may create a clerk's data collection protocol. The generated set of claimant-specific queries may also trigger an electronic records querying component (not shown) that facilitates the collection of the required data from EMR.

FIGS. 7A-7D illustrate an example medical provider's data collection protocol. The protocol lists the claimant-specific medical evidence queries to be satisfied from physician exams and laboratory tests. In the embodiment shown in FIGS. 7A-7D, the queries are grouped by category and sub-category. For example, the category "PHYSICAL EXAMINATION" shown in FIG. 7A includes sub-categories "VITAL SIGNS", "HEENT", "EYES", "SKIN", "HEART", and "MUSCULOSKELETAL SYSTEM". The grouping of categories and sub-categories presents the queries in a user-friendly order to the medical provider.

The medical provider uses the exam protocol to examine the claimant, and preferably enters collected medical evidence into the protocol. In one embodiment, the exam protocol is displayed to the medical provider on the screen of an electronic device such as a computer or a personal digital assistant, and the medical provider enters the collected medical evidence corresponding to each query into the electronic device. In another embodiment, the exam protocol is displayed to the medical provider in a paper report, and the medical provider enters the collected medical evidence on the paper report for a clerk to enter into a computer system.

The medical evidence collected by the medical provider is then stored into the disability claims benefits system 100. In one embodiment, for each generated claim-specific query and its FID, the corresponding medical evidence is simply inserted into the end of the FID. For example, for the FID "H047_SM500_T001" described above, if the medical provider determines that the range of motion is 90 degrees, then the FID becomes "H047_SM500_T001__90", with the last field within the FID storing the value of the medical evidence. In another embodiment, a table includes a "original FID" field that stores the FID of each query, and a "data value" that stores the medical evidence value of the corresponding FID. Other embodiments can also be implemented.

To replace or to supplement the physician's exam protocol, the component 136 may create a claimant questionnaire for those queries that can be satisfied by collecting answers directly from the claimant. FIGS. 8A-8E illustrate an example claimant questionnaire. The questionnaire can be filled out in paper or electronic form, by the claimant or by a clerk assisting the claimant. The questionnaire displays generated claimant-specific queries that can be satisfied by collecting answers from the claimant. The data entered into the questionnaire is then stored as collected medical evidence corresponding to the displayed queries. The data can be stored with the FIDs as described above, and preferably displayed to the physician for review or verification.

The clerk's data collection protocol displays generated claimant-specific queries that are to be collected from medical records. For each query, the protocol preferably displays an instruction to the clerk, for example "retrieve data from previous x-ray charts." The instructions can be retrieved from instructions stored in the knowledge library 118 that are associated with stored general medical evidence queries. In another embodiment, the system automatically notifies a custodian of medical records via email, voice mail or paper report to search for the medical evidence specified by the queries.

In yet another embodiment, the disability benefits claims system is connected to an electronic data storage that stores existing medical records as EMR, in, for example, a claimant database 160. The electronic data storage may comprise any type of computer-readable media, including hard disk drives, removable magnetic disks, removable optical disks, magnetic cassettes, flash memory cards, digital video disks, Bernoulli cartridges, random access memories, read-only memories, and the like. The claims system, via an electronic records querying component (not shown), may automatically search the data storage and collect required medical evidence from the EMR. If the claimant database 160 is encrypted, or if access to this database is otherwise restricted, the claims system may be configured to store the requisite authentication in order to access the database 160 freely. In another embodiment, the clerk or medical provider may be required to provide such authentication before the disability benefits claims system can access the database 160.

The claims system may communicate with the claimant database 160 by any of a variety of electronic communications methods well known to those of skill in the art, including over a local area network, a wide area network, the internet (preferably an encrypted internet connection), a phone line, etc. As is well understood by those of skill in the art, the terms "over" and "through" in reference to network access are used synonymously; thus, one may access data over the internet or through the internet. In a preferred embodiment, the claimant database 160 stores medical evidence in a format that may easily be correlated to the medical evidence queries. For example, the claimant database 160 may be formatted to a particular standard that is widely adopted, and which facilitates access by other applications that have also adopted the particular standard (e.g., Snomed). However, in other embodiments, the claims system may comprise sophisticated protocols for querying the database and for correlating the queries with meaningful evidence.

In order to improve the efficiency of the process, the claims system may first search the electronic data storage for medical evidence that is responsive to the generated claimant-specific queries. In one embodiment, the system may separate the exam queries from the medical record queries only after all possible claimant-specific queries have been answered using the evidence in the EMR. In another embodiment, as illustrated, the protocols 134, 136 may be created before the claimant database 160 is interrogated. In another, transitional embodiment, the claims system may simultaneously search the electronic data storage, and also provide a clerk's protocol according to which the claimant-specific queries may be answered from older, paper-based medical records.

Follow-Up Queries Based on Collected Medical Evidence

The query creation component 122 may create conditional claimant-specific queries. For example, if a required exam reveals an abnormal condition, then additional medical evidence may be required according to the rules collection 112 or according to medical knowledge 114. Such additional medical evidence queries are called conditional queries. The query whose medical evidence may trigger the conditional queries is called a triggering query. A triggering query may be associated with one or more sets of conditional queries. For example, a positive result of a laboratory test for a triggering query requires a first set of conditional queries, and a negative result may require a second set of conditional queries.

In one embodiment, the FID of a triggering query stored in the knowledge library 118 includes a list of the FIDs of the conditional queries. In another embodiment, each query is stored as an object in the knowledge library 118, and a triggering query object includes pointers to point to its conditional query objects. In yet another embodiment, the FID of a triggering query includes a flag code to indicate it is a triggering query. A triggering query table includes a first field that stores the FID of a triggering query and a second field that stores the FIDs of the corresponding conditional queries. In each embodiment, the knowledge library 118 may also store a triggering rule that indicates under what conditions the conditional queries are needed, for example "when the triggering query returns a positive test result" or "when the triggering query's medical evidence is not available."

Regardless of the storage embodiments, when the claimant-specific query creation component 122 generates a triggering query as a claimant-specific query, the conditional queries for the triggering query are preferably also generated as claimant-specific queries. The protocol creation components 134 and 136 identifies a triggering query, and preferably displays its corresponding conditional queries immediately following the triggering query. The medical provider's exam protocol, clerk's data collection protocol and claimant's questionnaire preferably include instructions to explain the triggering rules, for example "if this test result is positive, then answer the following questions."

The conditional queries can be displayed after the medical evidence for the triggering query is collected. For example, a medical provider's exam protocol is displayed to the medical provider on the screen of an electronic device, and the medical provider enters collected medical evidence into the electronic device. As the medical provider enters the medical evidence for a triggering query into the electronic device, the system 100 compares the entered medical evidence with the triggering query's triggering rule stored in the knowledge library 118, and displays the conditional queries according to the triggering rule. If the conditional queries are to be collected from physical exams, they are displayed on the electronic device or on an additional paper report. The conditional queries can also be displayed on a claimant questionnaire or clerk's data collection protocol, in electronic or paper form.

Creating Medical Report

Referring back to FIG. 1, after medical evidence is collected from physical examinations, laboratory tests, medical records and claimant questionnaire, the collected medical evidence is used by a medical report creation component 142 to create a medical report. FIGS. 9A-9B and FIG. 10 illustrate two example medical reports. FIGS. 9A-9B illustrate a sample narrative report. It includes collected medical evidence, for example medical history data and other data, in preferably a narrative form.

FIG. 10 illustrates a sample diagnostic code summary report. For a claimed right knee medical condition, the report displays a summary of claimant-specific queries and medical evidences, and corresponding rating codes such as "5010" and "5003". In one preferred embodiment described above, the FID for each query includes a category code, a rating code and a data query code. The rating code of the FID is thus displayed along with the collected medical evidence of the query. The report thus displays direct relationships of medical conditions, medical evidence and rating codes.

The medical report can be used by medical providers to review the claimant's medical evidence and to familiarize the medical providers with the associated rating codes. The report can also be used by rating personnel to review the claimant's medical evidence and associated rating codes. In some embodiments, medical reports can be used interchangeably with rating reports, which are described below in connection with FIGS. 11A-11H.

Depending on the insurance or disability program, reports of different formats can be generated to conform to the commonly accepted format of the particular program. For example, the medical evidence queries can be grouped by disease system on a report for a first insurance program, and grouped by module on another report for a second disability program.

Creating Rating Report

Referring back to FIG. 1, the rating report creation component 152 creates a rating report to assist rating personnel to adjudicate the insurance or disability requests of the claimant. FIGS. 11A-11H illustrate an example rating report, also called a rating decision toolkit.

In one embodiment, the rating report creation component 152 also recommends a rating decision to the rating personnel. The rating decision can be generated based on a set of mathematical formulas, a rule-based system, an expert system, a self-learning neural network, a fuzzy logic system, and so forth. The recommended rating decision can be generated in the form of a numerical value representing a disability percentage, a numerical value representing the insurance benefits dollar amount, a binary value representing a decision to grant or deny an insurance request, and so forth. As shown in FIG. 11C, for the rating code "5259", the component 152 recommends a V.A. rating of "10", i.e., a disability percentage of 10%. FIG. 11G displays a summary of all rating codes and corresponding recommended disability percentages, and a recommended combined disability percentage. The rating personnel can review the rating report and accept, reject or modify the recommended ratings.

The disclosed disability claims benefits system 100 can be implemented in a variety of computer languages, commercial applications and operating platforms. For example, the system can be implement in whole or in part in Visual Basis, C, SQL, and so forth.

Certain aspects, advantages and novel features of the invention have been described herein. Of course, it is to be understood that not necessarily all such aspects, advantages or features will be embodied in any particular embodiment of the invention. The embodiments discussed herein are provided as examples of the invention, and are subject to additions, alterations and adjustments. Therefore, the scope of the invention should be defined by the following claims.

What is claimed is:

1. A computer-implemented method of assisting medical evidence collection for adjudication of a medical disability request, the method comprising:

receiving from a claimant at least one claim of a medical condition;

generating a plurality of medical evidence queries based on and limited by the at least one claim and based on and limited by a disability rating rules collection;

displaying the generated medical evidence queries in a data collection protocol;

receiving medical evidence data responsive to the generated medical evidence queries from an electronic data storage;

determining, by a computer, a degree of disability based on the collected medical evidence data and on the disability rating rules collection; and generating, by a computer, a report comprising the degree of disability;

wherein the plurality of medical evidence queries is claim-type specific and is selected from a predetermined set of medical evidence queries, the set containing a greater number of queries than the number of queries in the plurality of queries; and wherein the generating the plurality of medical evidence queries comprises excluding queries, from the predetermined set of medical evidence queries, that are, based on the disability rating rules collection, not specific to the claim or claim type.

2. The method of claim 1, wherein the medical evidence data comprises responses to the generated medical evidence queries.

3. The method of claim 1, wherein the electronic data storage comprises electronic medical records.

4. The method of claim 1, wherein the receiving medical evidence data comprises receiving medical evidence data through a local area network.

5. The method of claim 1, wherein the receiving medical evidence data comprises receiving medical evidence data over the Internet.

6. The method of claim 1, wherein the receiving medical evidence data comprises receiving medical evidence data over an encrypted Internet connection.

7. The method of claim 1, wherein the receiving medical evidence data further comprises receiving medical evidence data collected by a medical provider.

8. The method of claim 7, wherein the receiving medical evidence data collected by a medical provider further comprises reviewing and extracting data from medical records.

9. The method of claim 7, wherein the receiving medical evidence data collected by a medical provider further comprises taking a medical history of the claimant.

10. The method of claim 9, wherein the medical history comprises at least one of a family history and a social history.

11. The method of claim 7, wherein the receiving medical evidence data collected by a medical provider further comprises receiving data from a physical exam.

12. The method of claim 7, wherein the receiving medical evidence data collected by a medical provider further comprises receiving data representative of laboratory tests.

13. The method of claim 7, wherein the receiving medical evidence data collected by a medical provider further comprises receiving data from radiological study results.

14. The method of claim 7, wherein the receiving medical evidence data collected by a medical provider further comprises receiving data from nuclear medicine laboratory results.

15. A computer-readable medium having computer-executable instructions stored thereon for performing the method of claim 1.

16. A computer-implemented method for facilitating adjudication of a medical disability request, the method comprising:

receiving medical evidence data concerning a claimant;

determining a degree of disability based on the medical evidence data and on a disability rating rules collection; and generating a disability rating report based on the medical evidence data;

wherein the medical evidence data is obtained by a method comprising the following steps:

receiving from the claimant at least one claim of a medical condition;

generating a plurality of medical evidence queries based on and limited by the at least one claim and based on and limited by the disability rating rules collection; and receiving answers to the generated medical evidence queries from an electronic data storage, said answers responsive to the medical evidence data;

wherein the disability rating report comprises a degree of disability; and wherein the plurality of medical evidence queries is claim-type specific and is selected from a predetermined set of medical evidence queries, the set containing a greater number of queries than the number of queries in the plurality of queries; and wherein the generating the plurality of medical evidence queries comprises excluding queries, from the predetermined set of medical evidence queries, that are, based on the disability rating rules collection, not specific to the claim or claim type.

17. The method of claim 16, wherein the electronic data storage comprises electronic medical records.

18. The method of claim 16, wherein the degree of disability comprises:

generating a recommended disability percentage based on the medical evidence data.

19. A computer system comprising a computer-readable medium having stored thereon computer-executable instructions configured to perform the method comprising:

receiving from a claimant at least one claim of a medical condition;

generating a plurality of medical evidence queries based on and limited by the at least one claim and based on and limited by a disability rating rules collection;

receiving medical evidence data responsive to the generated medical evidence queries from an electronic data storage;

determining a degree of disability based on the collected medical evidence data and on the disability rating rules collection; and generating a report comprising the degree of disability;

wherein the plurality of medical evidence queries is claim-type specific and is selected from a predetermined set of medical evidence queries, the set containing a greater number of queries than the number of queries in the plurality of queries; and wherein the generating the plurality of medical evidence queries comprises excluding queries, from the predetermined set of medical evidence queries, that are, based on the disability rating rules collection, not specific to the claim or claim type.

20. A computer-readable medium having stored thereon computer-executable instructions configured to perform the method comprising:

receiving from a claimant at least one claim of a medical condition;

generating a plurality of medical evidence queries based on and limited by the at least one claim and based on and limited by a disability rating rules collection;

receiving medical evidence data responsive to the generated medical evidence queries from an electronic data storage;

determining a degree of disability based on the collected medical evidence data and on the disability rating rules collection; and generating a report comprising the degree of disability;

wherein the plurality of medical evidence queries is claim-type specific and is selected from a predetermined set of medical evidence queries, the set containing a greater number of queries than the number of queries in the plurality of queries; and wherein the generating the plurality of medical evidence queries comprises excluding queries, from the predetermined set of medical evidence queries, that are, based on the disability rating rules collection, not specific to the claim or claim type.

21. A computer-implemented method of assisting medical evidence collection for adjudication of a medical disability request, the method comprising:

receiving from a claimant at least one claim of a medical condition;

generating a plurality of medical evidence queries based on and limited by the at least one claim and based on and limited by a disability rating rules collection;

receiving medical evidence data responsive to the generated medical evidence queries from an electronic data storage;

determining a degree of disability based on the collected medical evidence data and on the disability rating rules collection; and generating a report comprising the degree of disability;

wherein the plurality of medical evidence queries is claim-type specific and is selected from a predetermined set of medical evidence queries, the set containing a greater number of queries than the number of queries in the plurality of queries; and wherein the generating the plurality of medical evidence queries comprises excluding queries, from the predetermined set of medical evidence queries, that are, based on the disability rating rules collection, not specific to the claim or claim type.

* * * * *